US012274860B2

(12) United States Patent
Sasaki (10) Patent No.: US 12,274,860 B2
(45) Date of Patent: Apr. 15, 2025

(54) DRUG SOLUTION DELIVERY APPARATUS

(71) Applicant: TERUMO KABUSHIKI KAISHA, Tokyo (JP)

(72) Inventor: Shohei Sasaki, Chigasaki (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 917 days.

(21) Appl. No.: 17/400,560

(22) Filed: Aug. 12, 2021

(65) Prior Publication Data

US 2021/0369952 A1 Dec. 2, 2021

Related U.S. Application Data

(63) Continuation of application No. PCT/JP2019/033007, filed on Aug. 23, 2019.

(30) Foreign Application Priority Data

Feb. 18, 2019 (JP) ................................ 2019-026458

(51) Int. Cl.
*A61M 5/145* (2006.01)
*A61M 5/168* (2006.01)
*A61M 5/315* (2006.01)

(52) U.S. Cl.
CPC ........ *A61M 5/1456* (2013.01); *A61M 5/1684* (2013.01); *A61M 5/31528* (2013.01); *A61M 2205/14* (2013.01)

(58) Field of Classification Search
CPC ............ A61M 5/5086; A61M 5/14248; A61M 2205/8206; A61M 5/145;
(Continued)

(56) References Cited

U.S. PATENT DOCUMENTS 5,647,851 A * 7/1997 Pokras ................... A61M 5/20
604/131
2004/0064088 A1 4/2004 Gorman et al.
(Continued)

FOREIGN PATENT DOCUMENTS

CN 103228304 A 7/2013
JP 2016-198196 A 12/2016
(Continued)

OTHER PUBLICATIONS

International Searching Authority, "International Search Report," issued in connection with International Patent Application No. PCT/JP2019/033007, dated Nov. 12, 2019.
(Continued)

*Primary Examiner* — Joel M Attey
*Assistant Examiner* — Anna E Goldberg-Richmeier
(74) *Attorney, Agent, or Firm* — Foley & Lardner LLP (57) ABSTRACT

This drug solution delivery apparatus includes a pump main body, a cartridge main body having a plunger operation unit, and a controller for controlling a drive unit. The plunger operation unit has a slide nut and a rib for restricting movement of the slide nut. The drug solution delivery apparatus further includes an attachment detection sensor for detecting contact of the slide nut with the rib. The controller causes the drive unit to drive in reverse, and determines whether the cartridge main body is new or previously used on the basis of a detection signal of the attachment detection sensor.

12 Claims, 6 Drawing Sheets

(58) Field of Classification Search
CPC ...... A61M 2005/14506; A61M 5/1452; A61M 5/1456; A61M 5/14566; A61M 2005/14573; A61M 2205/70; A61M 2205/702; A61M 5/1684; A61M 5/31528; A61M 2205/14
See application file for complete search history.

(56) References Cited

U.S. PATENT DOCUMENTS

| | | | |
|---|---|---|---|
| 2014/0088507 A1* | 3/2014 | Matthew | A61M 5/14566 604/151 |
| 2017/0368269 A1* | 12/2017 | Kondo | A61M 5/1452 |
| 2019/0224419 A1 | 7/2019 | Pedersen et al. | |

FOREIGN PATENT DOCUMENTS

| | | |
|---|---|---|
| JP | 2018-157966 A | 10/2018 |
| JP | 2019-500992 A | 1/2019 |
| KR | 20140062789 A | 5/2014 |
| KR | 20140110496 A | 9/2014 |
| WO | WO-2015/098399 A1 | 7/2015 |
| WO | WO-2016/132937 A1 | 8/2016 |

OTHER PUBLICATIONS

International Searching Authority, "Written Opinion," issued in connection with International Patent Application No. PCT/JP2019/033007, dated Nov. 12, 2019.

Chinese Office Action issued in connection with CN Appl. Ser. No. 201980086635.9, dated Jan. 11, 2023.

* cited by examiner

DRUG SOLUTION DELIVERY APPARATUS

CROSS-REFERENCE TO RELATED APPLICATIONS

This application is a bypass continuation of PCT Appl. No. PCT/JP2019/033007, filed on Aug. 23, 2019, which claims priority to Japanese Appl. No. 2019-026458, filed on Feb. 18, 2019.

BACKGROUND

This disclosure relates to a drug solution delivery apparatus, for example, a drug solution delivery apparatus for performing continuous drug solution delivery such as an insulin pump.

In recent years, a treatment method for continuously delivering a drug solution into a living body of a patient by hypodermic injection, intravenous injection, or the like is performed. For example, as a treatment method for a diabetic patient, a treatment of continuously injecting a small amount of insulin into a living body of the patient is performed. In this treatment method, in order to deliver a drug solution (insulin) to a patient during the day, a portable drug solution delivery apparatus (so-called insulin pump) which is fixed to a living body or clothes of the patient and can be hold and carried is used. As one such portable drug solution delivery apparatus, there has been proposed a syringe pump including a syringe that stores a drug solution and a plunger driven inside the syringe.

WO2016/132937 discloses a drug solution delivery apparatus including a disposable unit that can be thrown away and a reusable unit detachably provided in the disposable unit. A drug solution storage unit filled with a drug solution, a plunger member, a plunger operation unit, and the like are disposed in the disposable unit, which is a cartridge main body. A drive unit is disposed in the reusable unit, which is a pump main body.

WO2016/132937 discloses that a contact-type sensor that detects a remaining amount of the drug solution in the drug solution storage unit by being pressed by a slide nut of the plunger operation unit. When the slide nut presses the sensor, the remaining amount of the drug solution is detected, and it is determined whether the cartridge main body has been previously used.

SUMMARY

However, when the cartridge main body is detached from the pump main body in front of a position where the slide nut presses the sensor, the slide nut does not press the sensor even when a previously used cartridge main body is mounted on the pump main body again. As a result, there are problems that the cartridge is not correctly recognized as a used cartridge, and a notification of the remaining amount of the drug solution in the drug solution storage unit and replacement time of the cartridge main body cannot be correctly provided.

In consideration of the above problems, an object of this disclosure is to provide a drug solution delivery apparatus capable of accurately determining whether a cartridge main body was previously used when the cartridge main body is mounted on a pump main body.

According to one embodiment, a drug solution delivery apparatus according includes a pump main body in which a drive unit is provided, a cartridge main body detachably mounted on the pump main body, and a controller configured to control the drive unit. The cartridge main body includes a drug solution storage unit filled with a drug solution, a plunger member configured to push out the drug solution filled in the drug solution storage unit, and a plunger operation unit configured to operate movement of the plunger member. The plunger operation unit includes a feed screw shaft configured to be rotated by the drive unit, an axial direction of the plunger operation unit being parallel to a moving direction of the plunger member, a slide nut configured to be screwed to the feed screw shaft to be movable along the axial direction of the feed screw shaft, and to be interlocked with the plunger member, and a rib provided on a side opposite to a side on which the slide nut approaches the plunger member and configured to restrict movement of the slide nut.

At least one of the pump main body and the cartridge main body is provided with an attachment detection sensor configured to detect that the slide nut attaches to the rib.

When the cartridge main body is mounted on the pump main body, the controller causes the drive unit to rotate in a direction opposite to a forward direction in which the slide nut is interlocked with the plunger member, and determines whether the cartridge main body is new or has been used based on a detection signal of the attachment detection sensor.

According to the drug solution delivery apparatus of this disclosure, it is possible to accurately determine whether the cartridge main body is a used cartridge main body when the cartridge main body is mounted on the pump main body.

DETAILED DESCRIPTION

Hereinafter, an embodiment of a drug solution delivery apparatus according to this disclosure will be described with reference to FIGS. 1 to 6. In the drawings, common members are denoted by the same reference numerals. This disclosure is not limited to the following embodiment.

1. Embodiment

1-1. Configuration of Drug Solution Delivery Apparatus

First, an example configuration of the drug solution delivery apparatus according to the embodiment will be described with reference to FIGS. 1 to 3.

Figure 1:
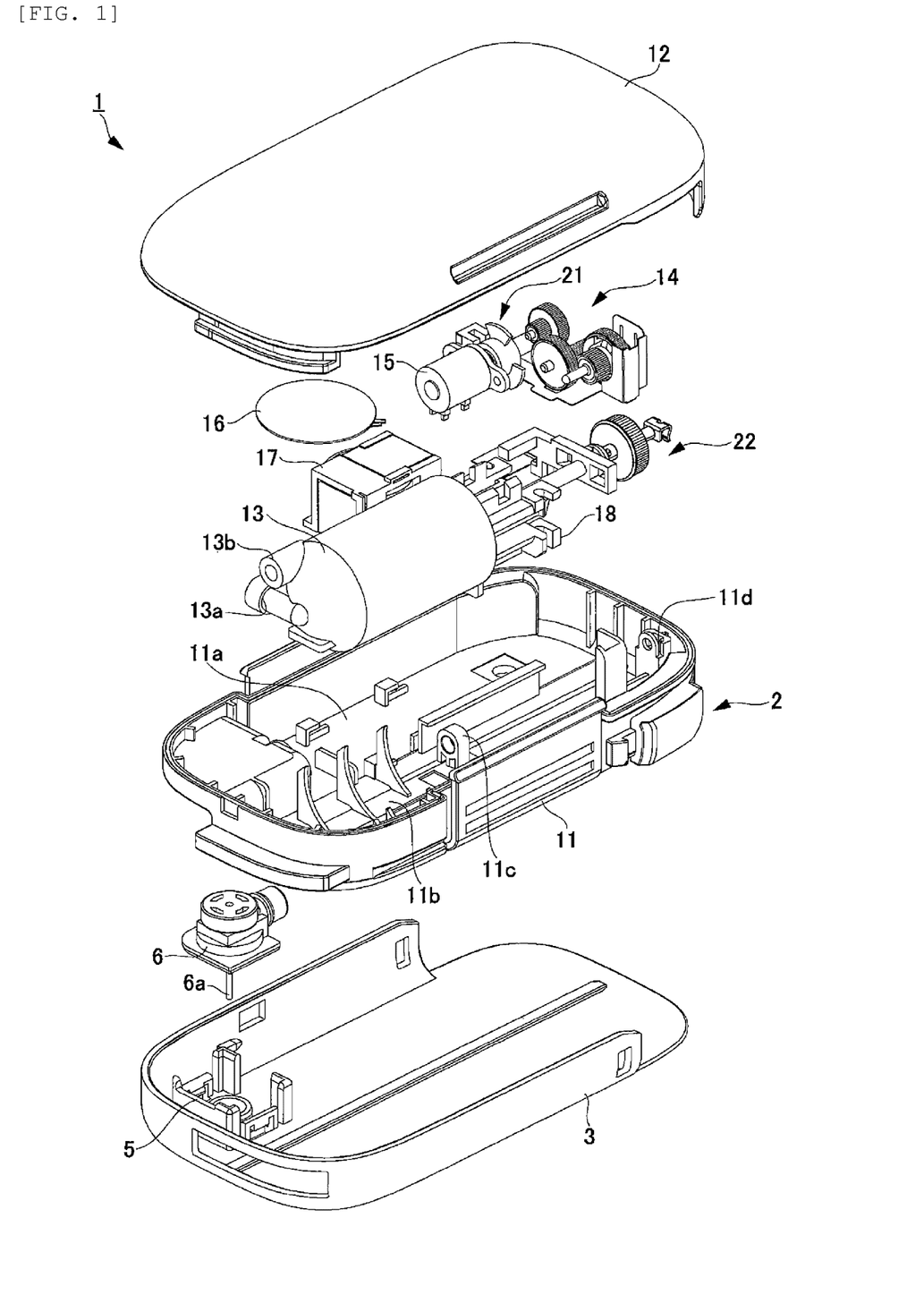
FIG. 1 is an exploded perspective view showing a drug solution delivery apparatus according to an embodiment.

FIG. 1 is an exploded perspective view showing the drug solution delivery apparatus. FIG. 2 is a plan view showing the drug solution delivery apparatus.

The apparatus shown in FIG. 1 is a portable insulin pump for continuously delivering a drug solution into a living body of a patient, such as a patch type or tube type insulin pump, or another portable drug solution delivery apparatus. A drug solution delivery apparatus 1 includes a drug solution delivery unit 2, a cradle device 3 to which the drug solution delivery unit 2 is detachably mounted, and a connection port 6 mounted on the cradle device 3.

The cradle device 3 is provided with a mounting unit 5 on which the connection port 6 is mounted. The connection port 6 has a cannula 6a. The cradle device 3 is appended to skin of a patient. The connection port 6 is mounted on the mounting unit 5 by using a puncture mechanism (not shown). When the connection port 6 is mounted on the mounting unit 5 of the cradle device 3, the cannula 6a protrudes from a side of the cradle device 3 that is opposite to a side on which the drug solution delivery unit 2 is mounted, so that the cannula 6a is punctured and indwelled in a living body.

When the drug solution delivery unit 2 is mounted on the cradle device 3 in a state in which the connection port 6 is mounted on the cradle device 3, the connection port 6 is accommodated in a rear surface accommodation portion of a cartridge main body 11 of the drug solution delivery unit 2. The cartridge main body 11 will be described later. Then, the connection port 6 is connected to a liquid delivering pipe 19 of the drug solution delivery unit 2 to be described later.

The drug solution delivery unit 2 includes the cartridge main body 11 and a pump main body 12. The drug solution delivery unit 2 is formed by detachably bonding the cartridge main body 11 and the pump main body 12.

The drug solution delivery unit 2 further includes a drug solution storage unit 13, a transmission mechanism 14, a drive motor 15 (which is an example of a drive unit), a notification unit 16, and a power supply unit 17. The drug solution delivery unit 2 further includes a plunger member 18 that pushes out a drug solution filled in the drug solution storage unit 13, the liquid delivering pipe 19, a rotation detection unit 21, and a plunger operation unit 22 that operates the plunger member 18.

The cartridge main body 11 is formed in a substantially rectangular parallelepiped shape of which the inside is hollow and one surface is open. The drug solution storage unit 13, the power supply unit 17, the plunger member 18, the liquid delivering pipe 19, and the plunger operation unit 22 that operates the plunger member 18 are attached to the cartridge main body 11. The cartridge main body 11 includes a first accommodation portion 11a and a second accommodation portion 11b. The power supply unit 17 is disposed in the first accommodation portion 11a.

The drug solution storage unit 13, the plunger member 18, and the plunger operation unit 22 are accommodated in the second accommodation portion 11b. The second accommodation portion 11b is provided with a first bearing portion 11c and a second bearing portion 11d. The first bearing portion 11c and the second bearing portion 11d protrude from a bottom surface portion of the second accommodation portion 11b toward the opening. A feed screw shaft 22b of the plunger operation unit 22 is rotatably supported by the first bearing portion 11c. A shaft portion 23a of an operation gear 23 in the plunger operation unit 22 is rotatably supported by the second bearing portion 11d.

The pump main body 12 is formed in a substantially flat plate shape. The pump main body 12 covers the first accommodation portion 11a and the second accommodation portion 11b formed in the cartridge main body 11, and closes the opening of the cartridge main body 11. The transmission mechanism 14, the drive motor 15, the notification unit 16, and the rotation detection unit 21 are attached to the pump main body 12.

When the cartridge main body 11 is mounted on the pump main body 12, the drive motor 15 and the rotation detection unit 21 are disposed in the first accommodation portion 11a of the cartridge main body 11, and the transmission mechanism 14 is disposed in the first accommodation portion 11a and the second accommodation portion 11b of the cartridge main body 11.

The drug solution storage unit 13 (container) is formed in a tubular shape of which one end in an axial direction is closed and the other end in the axial direction is open. The drug solution is stored in a cylinder hole 13c of the drug solution storage unit 13. A liquid delivering port 13a and a filling port 13b are formed at the one end portion of the drug solution storage unit 13 in the axial direction.

The liquid delivering port 13a is connected to the liquid delivering pipe 19. An end portion of the liquid delivering pipe 19 that is opposite to the liquid delivering port 13a is connected to the connection port 6. The cannula 6a of the connection port 6 is punctured and indwelled in the living body of the patient. Then, the drug solution stored in the cylinder hole 13c of the drug solution storage unit 13 is discharged from the liquid delivering port 13a, passes through the liquid delivering pipe 19 and the connection port 6, and is delivered to the patient.

A filling device (not shown) is connected to the filling port 13b. Then, the drug solution is filled into the cylinder hole 13c of the drug solution storage unit 13 via the filling port 13b.

The plunger member 18 is slidably inserted into the cylinder hole 13c of the drug solution storage unit 13. The plunger member 18 includes a gasket 18a and a shaft portion 18b. The gasket 18a is slidably disposed in the cylinder hole 13c of the drug solution storage unit 13. The gasket 18a moves while being in close contact with an inner peripheral surface of the cylinder hole 13c of the drug solution storage unit 13 in a liquid-tight manner.

A shape of a tip portion of the gasket 18a corresponds to a shape of the cylinder hole 13c of the drug solution storage unit 13 on one end side in the axial direction. Accordingly, when the gasket 18a moves to the one end side of the drug solution storage unit 13 in the axial direction, the drug solution filled in the drug solution storage unit 13 can be discharged from the liquid delivering port 13a without waste.

The shaft portion 18b is provided on a side of the gasket 18a that is opposite to the tip portion. The shaft portion 18b extends outward from an opening formed at the other end of the drug solution storage unit 13 in the axial direction. An interlock portion 18c interlocked with a slide nut 22c, which will be described later, of the plunger operation unit 22 is provided at an end portion of the shaft portion 18b that is opposite to the gasket 18a. When the interlock portion 18c is interlocked with the slide nut 22c and the plunger operation unit 22 is driven, the plunger member 18 moves along the axial direction of the drug solution storage unit 13.

The plunger operation unit 22 includes the operation gear 23, the feed screw shaft 22b, the slide nut 22c, and a rib 24. The operation gear 23 meshes with a gear of the transmission mechanism 14 to be described later. One end of the shaft portion 23a of the operation gear 23 is connected to an end portion of the feed screw shaft 22b in the axial direction.

The other end of the shaft portion 23a of the operation gear 23 is rotatably supported by the second bearing portion 11d.

The feed screw shaft 22b is rotatably supported by the first bearing portion 11c. The feed screw shaft 22b is disposed such that an axial direction thereof is parallel to the shaft portion 18b. That is, the feed screw shaft 22b is disposed parallel to the moving direction of the plunger member 18. The slide nut 22c is screwed to the feed screw shaft 22b.

When the slide nut 22c is accommodated in the cartridge main body 11, rotation of the feed screw shaft 22b around a circumferential direction is restricted. Accordingly, when the operation gear 23 rotates and the feed screw shaft 22b rotates, the slide nut 22c moves along the axial direction of the feed screw shaft 22b. After the interlock portion 18c of the plunger member 18 is engaged with the slide nut 22c, with the rotation of the feed screw shaft 22b, the plunger member 18 moves along the axial direction of the feed screw shaft 22b together with the slide nut 22c. A drive force of the drive motor 15 is transmitted to the plunger operation unit 22 via the transmission mechanism 14.

The rib 24 is provided at an interlock place between the feed screw shaft 22b and the operation gear 23. That is, the rib 24 is provided on a side opposite to a side on which the slide nut 22c approaches the interlock portion 18c. With the rotation of the feed screw shaft 22b, when the slide nut 22c moves in a direction away from the interlock portion 18c, that is, to the end portion of the feed screw shaft 22b in the axial direction, the slide nut 22c attaches to the rib 24. When the slide nut 22c attaches to the rib 24, the movement of the slide nut 22c in the axial direction is restricted. As a result, the drive motor 15 connected to the plunger operation unit 22 via the transmission mechanism 14 is out of synchronization.

In the new cartridge main body 11 before being attached to the pump main body 12, the slide nut 22c is disposed at a predetermined interval T1 with respect to the rib 24.

As the drive motor 15, for example, a stepping motor is applied. Then, the drive motor 15 rotates to perform driving based on a drive signal from a calculation unit 101 (controller) to be described later.

In a state in which the opening of the cartridge main body 11 is closed by the pump main body 12, the drive motor 15 is connected to an electrode of the power supply unit 17 accommodated in the cartridge main body 11 so that power is supplied to the drive motor 15. A drive shaft 15a of the drive motor 15 is provided with the rotation detection unit 21 that detects rotation of the drive shaft 15a.

Figure 3:
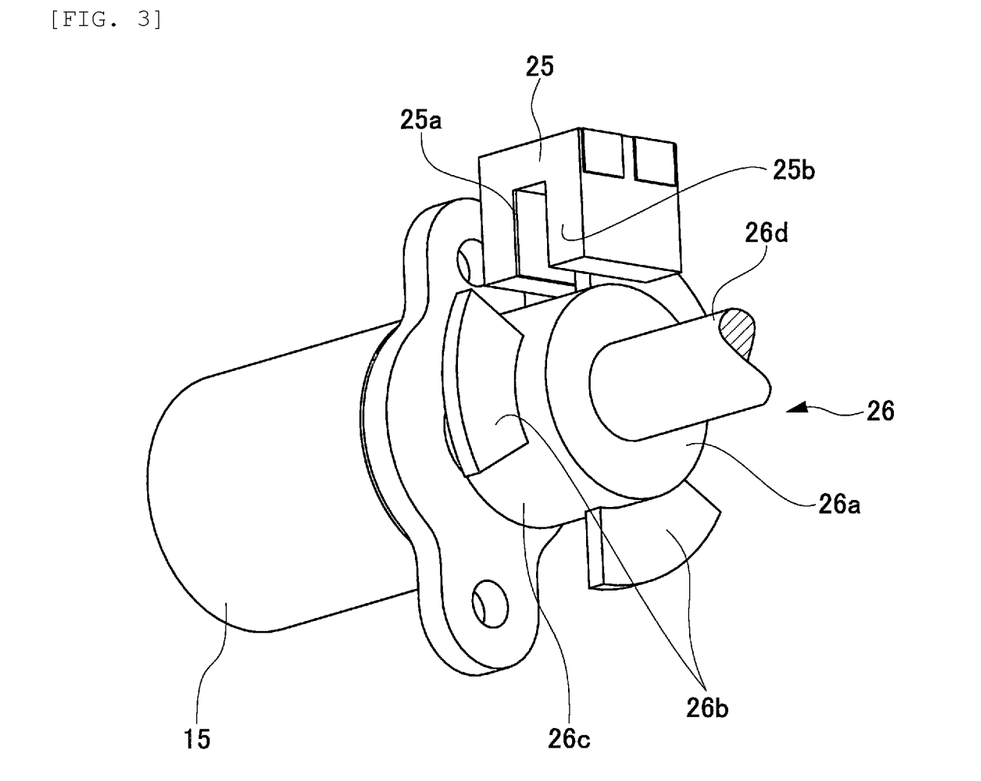
FIG. 3 is a perspective view showing a rotation detection unit of the drug solution delivery apparatus according to the embodiment.

FIG. 3 is a perspective view showing the rotation detection unit 21. As shown in FIG. 3, the rotation detection unit 21, which is an example of an attachment detection sensor, is a rotary encoder including a detection sensor 25 and a rotary body 26. The rotary body 26 includes a rotary body main body portion 26a fixed to the drive shaft 15a of the drive motor 15, three shielding plates 26b provided on the rotary body main body portion 26a, and a shaft portion 26d provided on the rotary body main body portion 26a.

The rotary body main body portion 26a is formed in a substantially columnar shape. The rotary body main body portion 26a rotates in synchronization with the rotation of the drive shaft 15a. The shaft portion 26d protrudes to a side opposite to the drive shaft 15a in an axial direction of the rotary body main body portion 26a. The shaft portion 26d is provided with a gear (not shown), and meshes with the gear of the transmission mechanism 14.

The three shielding plates 26b are provided at equal angular intervals on an outer peripheral surface of the rotary body main body portion 26a. Therefore, three slits 26c are defined at equal angular intervals on a peripheral edge of the rotary body main body portion 26a by the three shielding plates 26b.

The detection sensor 25 is disposed in the pump main body 12. The detection sensor 25 is an optical sensor including a light emitting unit 25a that emits light and a light receiving unit 25b that receives the light emitted from the light emitting unit 25a. The light emitted from the light emitting unit 25a is blocked by the shielding plates 26b of the rotary body 26 or passes through the slits 26c of the rotary body 26.

As described above, the three shielding plates 26b and the three slits 26c are formed on the rotary body 26. Therefore, when the drive shaft 15a of the drive motor 15 performs one rotation, that is, when the rotary body 26 performs one rotation, the light receiving unit 25b of the detection sensor 25 detects a pulse signal in which one set including "dark" indicating that the light is blocked by the shielding plates 26b and "bright" indicating that the light passing through the slits 26c is detected is repeated three times. Therefore, the detection sensor 25 detects rotation of the drive motor 15.

The number of the shielding plates 26b is not limited to three, and two or four and more shielding plates 26b may be provided. Accordingly, the pulse signal generated when the rotary body 26 performs one rotation appropriately changes according to the number of the shielding plates 26b and the slits 26c.

The detection sensor 25 outputs detected rotation information on the drive motor 15 to the calculation unit 101 (controller) to be described later.

Figure 2:
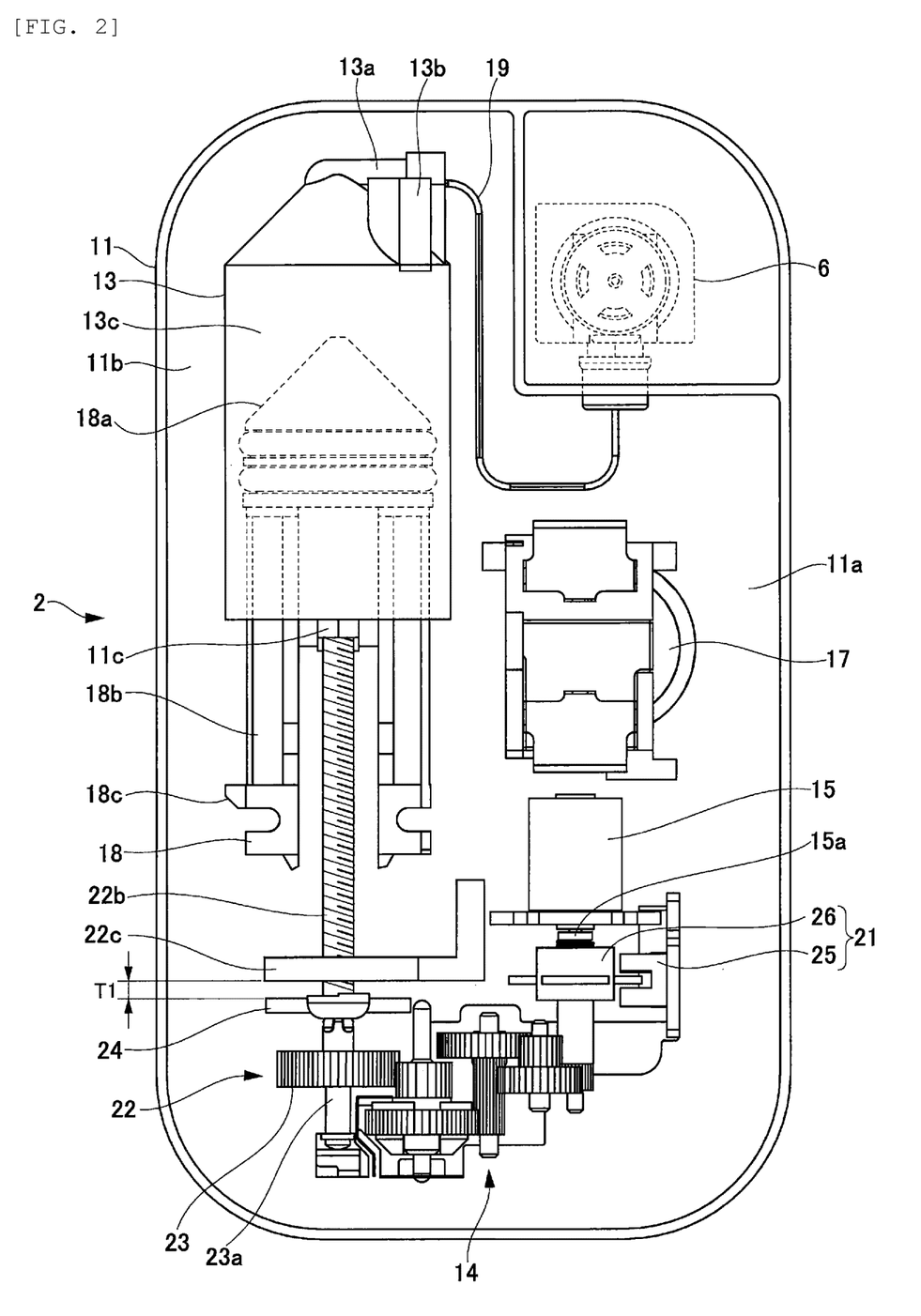
FIG. 2 is a plan view showing the drug solution delivery apparatus according to the embodiment.

As shown in FIGS. 1 and 2, the transmission mechanism 14 is connected to the drive shaft 15a of the drive motor 15 via the rotation detection unit 21. The transmission mechanism 14 transmits the drive force (rotation) of the drive motor 15 to the plunger operation unit 22. The transmission mechanism 14 is constituted by a plurality of gears. When the drive motor 15 performs driving, the plurality of gears constituting the transmission mechanism 14 rotate so that the drive force of the drive motor 15 is transmitted to the operation gear 23. Therefore, the plunger member 18 is operated, and the drug solution stored in the drug solution storage unit 13 is pushed out by the gasket 18a.

The notification unit 16 is connected to the calculation unit 101. The notification unit 16 is driven by an instruction from the calculation unit 101 (controller) when a malfunction occurs in the drug solution delivery apparatus 1, when a blockage is detected, or the like, and outputs an alarm. As the alarm output by the notification unit 16, for example, vibration, sound, or the like may be output alone, or vibration, sound, or the like may be used and output in combination.

The power supply unit 17 is for supplying power to each component constituting the drug solution delivery apparatus 1. The power supply unit 17 includes, for example, a battery 17a, a battery box that accommodates the battery 17a, and a switch that turns on and off the supply of power from the battery. When the cartridge main body 11 and the pump main body 12 are overlapped with each other, the power supply unit 17 comes into contact with a connection terminal (not shown) provided in the pump main body 12.

1-2. Control System of Drug Solution Delivery Apparatus

Next, a control system of the drug solution delivery apparatus 1 will be described with reference to FIG. 4.

Figure 4:
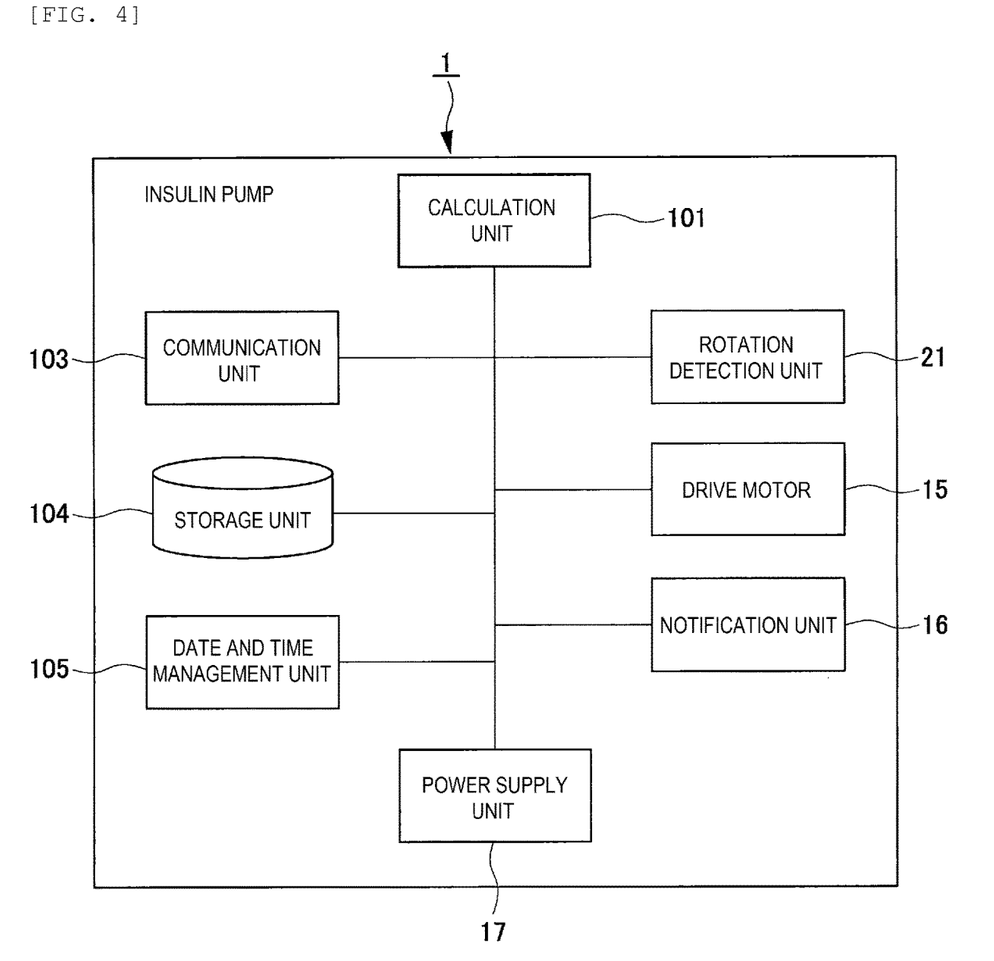
FIG. 4 is a block diagram showing a control system of the drug solution delivery apparatus according to the embodiment.

FIG. 4 is a block diagram showing the control system of the drug solution delivery apparatus 1.

As shown in FIG. 4, the drug solution delivery apparatus 1 includes the drive motor 15, the rotation detection unit 21, the notification unit 16, and the power supply unit 17, which are described above. The drug solution delivery apparatus 1 further includes the calculation unit 101 which is an example of a controller, a communication unit 103, a storage unit 104, and a date and time management unit 105.

The drive motor 15, the rotation detection unit 21, the notification unit 16, the power supply unit 17, the communication unit 103, the storage unit 104, and the date and time management unit 105 are connected to the calculation unit 101.

The rotation information on the drive motor 15 detected by the detection sensor 25 (see FIG. 3) of the rotation detection unit 21 is output to the calculation unit 101. The calculation unit 101 determines whether the slide nut 22c and the interlock portion 18c are interlocked with each other based on the rotation information on the drive motor 15 detected by the rotation detection unit 21. The driving of the drive motor 15 is controlled by the calculation unit 101.

The communication unit 103 is connected to a controller (not shown) for operating the drug solution delivery apparatus 1, an external portable information processing terminal, or a personal computer (PC) via a wired or wireless network. The communication unit 103 receives operation information operated by a user via the controller (not shown), the portable information processing terminal, or the like, or measurement data measured by an external device. Then, the communication unit 103 outputs the received operation information and measurement data to the calculation unit 101.

The communication unit 103 is controlled by the calculation unit 101 to output blockage information, information related to an amount of the drug solution stored in the drug solution storage unit 13, and various kinds of information related to the drug solution delivery apparatus 1, such as a delivery pattern, to the controller (not shown), the portable information processing terminal, or the like.

The storage unit 104 is a unit that stores various types of data. The storage unit 104 stores a control program for controlling a delivery profile or the like indicating a delivery pattern for delivering the drug solution, threshold value data used in a drug solution delivery preparation operation for the blockage detection, and the like. The storage unit 104 further stores information received by the communication unit 103, the rotation information on the drive motor 15 detected by the rotation detection unit 21, and the like. The storage unit 104 outputs the control program stored in advance and the rotation information received from other processing units to the calculation unit 101.

A rotation amount of the drive motor 15 until the slide nut 22c attaches to the rib 24 is stored in the storage unit 104.

The date and time management unit 105 is a program part for performing date and time management, may be mounted on a general microcomputer, and outputs date and time information based on a command from the calculation unit 101. The date and time management unit 105 is supplied with power even when the power is off, thereby outputting accurate date and time information.

Programs for controlling various devices such as the drive motor 15, the communication unit 103, the storage unit 104, and the date and time management unit 105 are mounted on the calculation unit 101. The calculation unit 101 controls various operations of the drug solution delivery apparatus 1 based on the programs. The calculation unit 101 receives the rotation information on the drive motor 15 detected by the rotation detection unit 21, and the like. The calculation unit 101 stores the received information in the storage unit 104.

The calculation unit 101 sets the drive signal for causing the drive motor 15 to rotate based on the rotation information. The calculation unit 101 causes the drive motor 15 to rotate based on the set drive signal.

In addition, the calculation unit 101 causes the drive motor 15 to rotate based on the delivery profile indicating the delivery pattern of the drug solution that is stored in the storage unit 104. As a result, the drug solution based on the predetermined delivery profile is delivered to the user. The calculation unit 101 includes, for example, a central processing unit (CPU), a random access memory (RAM), and a read only memory (ROM), which are not shown here. The read only memory (ROM) may be the storage unit 104.

2. New Product Determination Operation of Cartridge Main Body of Drug Solution Delivery Apparatus Next, a new product determination operation of the cartridge main body 11 performed when the cartridge main body 11 is mounted on the pump main body 12 of the drug solution delivery apparatus 1 having the above-described configuration will be described with reference to FIGS. 5 and 6.

2-1. First Operation Example

Figure 5:
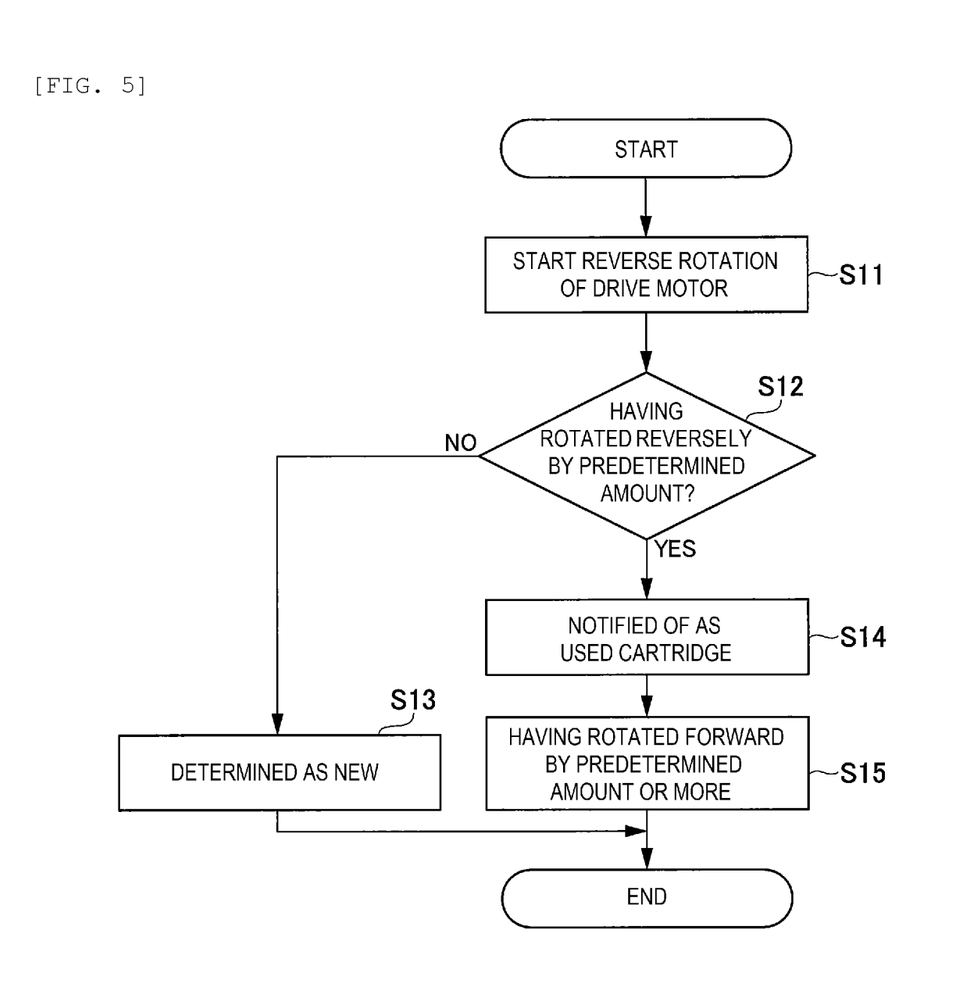
FIG. 5 is a flowchart showing a first operation example of a new product determination operation of a cartridge main body in the drug solution delivery apparatus according to the embodiment.

FIG. 5 is a flowchart showing a first operation example of the new product determination operation.

As shown in FIG. 5, when the cartridge main body 11 is mounted on the pump main body 12, the calculation unit 101 controls the drive motor 15 to start a reverse rotation of the drive motor 15 (step S11). The reverse rotation of the drive motor 15 in the processing of step S11 is performed in a direction in which the slide nut 22c moves in a direction opposite to a direction in which the slide nut 22c approaches the drug solution storage unit 13.

Next, the calculation unit 101 determines whether the drive motor 15 has rotated by a predetermined amount based on the rotation information detected by the rotation detection unit 21 (step S12). The number of rotations of the drive motor 15 performed in the processing of step S12 is set to be equal to or greater than the number of rotations of the drive motor 15 performed until the slide nut 22c attaches to the rib 24.

When the slide nut 22c attaches to the rib 24, the movement of the slide nut 22c is restricted, the drive motor 15 is out of synchronization, and an error occurs in the rotation information detected by the rotation detection unit 21. Therefore, in the processing of step S12, the calculation unit 101 determines that the drive motor 15 has not rotated by the predetermined amount (determined as NO in step S12). The calculation unit 101 determines the cartridge main body 11 mounted on the pump main body 12 as a new product (step S13). The calculation unit 101 notifies, via the communication unit 103, the controller (not shown), the external portable information processing terminal, or the like that the cartridge main body 11 is a new product.

In contrast, when the cartridge main body 11 has been used, the slide nut 22c is separated from the rib 24, and an interval between the slide nut 22c and the rib 24 is larger than the interval T1 between the slide nut 22c and the rib 24 in the new cartridge main body 11. Therefore, when the cartridge main body 11 has been used, the slide nut 22c does not attach to the rib 24 even when the drive motor 15 has rotated by the predetermined amount.

Therefore, in the processing of step S12, when the calculation unit 101 determines that the drive motor 15 has rotated by the predetermined amount (determined as YES in step S12), the calculation unit 101 determines that the mounted cartridge main body 11 has been previously used. The calculation unit 101 notifies, via the communication unit 103, the controller (not shown), the external portable information processing terminal, or the like that the cartridge main body 11 has been previously used (step S14).

Next, the calculation unit 101 controls the drive motor 15 to rotate in the direction in which the slide nut 22c is separated from the rib 24, that is, forward by the predetermined amount or more (step S15). Accordingly, it is possible to prevent an interval between the slide nut 22c and the rib 24 in the used cartridge main body 11 from matching the interval T1 between the slide nut 22c and the rib 24 in the new cartridge main body 11.

Through the above-described steps, the new product determination operation of the cartridge main body 11 in the drug solution delivery apparatus 1 is completed. According to the drug solution delivery apparatus 1 of the present embodiment, it is possible to reliably distinguish between a previously used cartridge main body 11 and a new cartridge main body 11.

2-1. Second Operation Example

Figure 6:
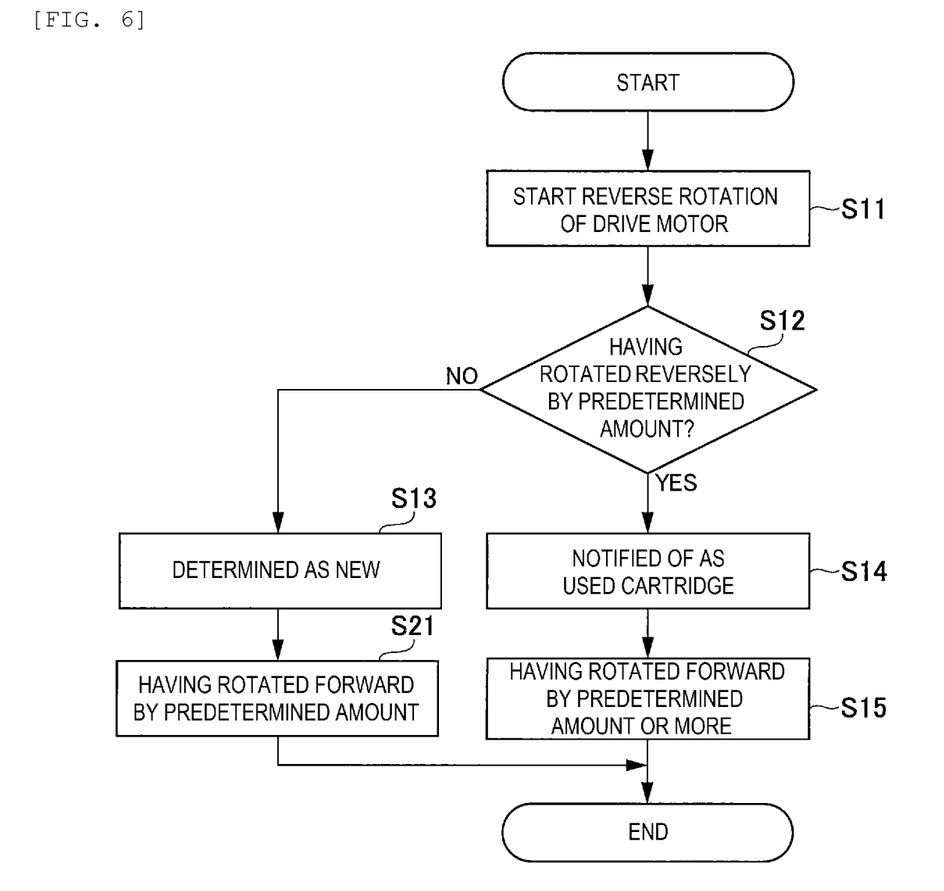
FIG. 6 is a flowchart showing a second operation example of the new product determination operation of the cartridge main body in the drug solution delivery apparatus according to the embodiment.

FIG. 6 is a flowchart showing a second operation example of the new product determination operation.

In the first operation example shown in FIG. 5, when the calculation unit 101 determines a new product in the processing of step S13, the new product determination operation is ended. In contrast, in the second operation example shown in FIG. 6, after the new product determination is performed in the processing of step S13, the calculation unit 101 controls the drive motor 15 to perform forward rotation by a predetermined amount (step S21). Accordingly, the slide nut 22c of the cartridge main body 11 determined as a new product returns to an initial position shown in FIG. 2. As a result, when the drug solution delivery preparation operation or a drug solution delivery operation is performed after the new product determination operation is performed, the slide nut 22c can be started from the initial position.

Hereinabove, the embodiment of this disclosure has been described including the operations and effect thereof. However, the drug solution delivery apparatus of this disclosure is not limited to the above-described embodiment, and various modifications can be made without departing from the spirit of the invention described in the claims.

In the embodiment described above, an example in which an insulin pump for delivering insulin is applied as the drug solution delivery apparatus is described, but the invention is not limited thereto. As the drug solution to be delivered, other various drug solutions may be used, such as an analgesic drug, an anti-cancer therapeutic drug, an HIV drug, an iron chelate drug, and a pulmonary hypertension therapeutic drug.

In addition, in the above-described embodiment, an example in which the rotation detection unit 21 is used as the attachment detection sensor and the calculation unit 101 determines whether the slide nut 22c attaches to the rib 24 is described, but the invention is not limited thereto. As the attachment detection sensor, for example, a deflection sensor that detects deflection of the cartridge main body 11 may be used. When the slide nut 22c attaches to the rib 24, the cartridge main body 11 accommodating the slide nut 22c is deflected. The calculation unit 101 determines whether the slide nut 22c attaches to the rib 24 based on the deflection of the cartridge main body 11 detected by the deflection sensor.

As the attachment detection sensor, various other sensors such as a mechanical pressure sensor and an optical sensor may be used. A position of the slide nut 22c or the attachment of the slide nut 22c to the rib 24 may be detected by the pressure sensor or the optical sensor, and the calculation unit 101 may determine whether the slide nut 22c attaches to the rib 24 based on a detection signal.

REFERENCE NUMERAL LIST

1 . . . drug solution delivery apparatus, 2 . . . drug solution delivery unit, 3 . . . cradle device, 5 . . . mounting unit, 6 . . . connection port, 6a . . . cannula, 11 . . . cartridge main body, 11c . . . first bearing portion, 11d . . . second bearing portion, 12 . . . pump main body, 13 . . . drug solution storage unit, 14 . . . transmission mechanism, 15 . . . drive motor (drive unit), 15a . . . drive shaft, 16 . . . notification unit, 17 . . . power supply unit, 18 . . . plunger member, 18a . . . gasket, 18b . . . shaft portion, 18c . . . interlock portion, 19 . . . liquid delivering pipe, 21 . . . rotation detection unit (attachment detection sensor), 22 . . . plunger operation unit, 22b . . . feed screw shaft, 22c . . . slide nut, 23 . . . operation gear, 24 . . . rib, 25 . . . detection sensor, 25a . . . light emitting unit, 25b . . . light receiving unit, 26 . . . rotary body, 26a . . . rotary body main body portion, 26b . . . shielding plate, 26c . . . slit, 101 . . . calculation unit (controller), 104 . . . storage unit

The invention claimed is:

1. A drug solution delivery apparatus comprising:
a pump main body comprising a drive unit;
a cartridge main body detachably mounted on the pump main body; and
a controller configured to control the drive unit, wherein:
the cartridge main body comprises:
a drug solution storage unit filled with a drug solution,
a plunger member configured to push out the drug solution filled in the drug solution storage unit, and
a plunger operation unit configured to operate movement of the plunger member, the plunger operation unit comprising:
a feed screw shaft configured to be rotated by the drive unit, an axial direction of the feed screw shaft being parallel to a moving direction of the plunger member,
a slide nut configured to be screwed to the feed screw shaft to be movable along the axial direction of the feed screw shaft, and to be interlocked with the plunger member, and
a rib located on a side opposite to a side on which the slide nut approaches the plunger member and configured to restrict movement of the slide nut,
at least one of the pump main body or the cartridge main body comprises an attachment detection sensor configured to detect that the slide nut is attached to the rib, and
the controller is programmed such that, when the cartridge main body is mounted on the pump main body, the controller causes the drive unit to rotate in a direction opposite to a forward direction in which the slide nut is interlocked with the plunger member, and determines whether the cartridge main body is a new cartridge main body or a previously used cartridge main body based on a detection signal of the attachment detection sensor.

2. The drug solution delivery apparatus according to claim 1, wherein:
in the new cartridge main body, the slide nut is disposed at a predetermined interval from the rib, and
when the cartridge main body is mounted on the pump main body, the controller causes the drive unit to rotate in a reverse direction by a predetermined amount.

3. The drug solution delivery apparatus according to claim 2, wherein:
the controller is programmed such that the number of rotations by which the drive unit is caused to rotate is set to be equal to or greater than the number of rotations of the drive unit until the slide nut attaches to the rib.

4. The drug solution delivery apparatus according to claim 2, wherein:
the controller is programmed such that, when it is determined that the cartridge main body is the previously used cartridge main body, the controller causes the drive unit to rotate in a forward direction by a predetermined amount or more.

5. The drug solution delivery apparatus according to claim 2, wherein:
the controller is programmed such that, when it is determined that the cartridge main body is the new cartridge main body, the controller causes the drive unit to rotate in a forward direction by a predetermined amount.

6. The drug solution delivery apparatus according to claim 1, wherein:
the attachment detection sensor is configured to detect rotation of the drive unit.

7. A drug solution delivery apparatus comprising:
a pump main body comprising a drive motor;
a cartridge main body detachably mounted on the pump main body; and
a controller configured to control the drive motor, wherein:
the cartridge main body comprises:
a drug solution container filled with a drug solution,
a plunger member configured to push out the drug solution filled in the drug solution container, and
a plunger operation unit configured to operate movement of the plunger member, the plunger operation unit comprising:
a feed screw shaft configured to be rotated by the drive motor, an axial direction of the feed screw shaft being parallel to a moving direction of the plunger member,
a slide nut configured to be screwed to the feed screw shaft to be movable along the axial direction of the feed screw shaft, and to be interlocked with the plunger member, and
a rib located on a side opposite to a side on which the slide nut approaches the plunger member and configured to restrict movement of the slide nut,
at least one of the pump main body or the cartridge main body comprises an attachment detection sensor configured to detect that the slide nut is attached to the rib, and
the controller is programmed such that, when the cartridge main body is mounted on the pump main body, the controller causes the drive motor to rotate in a direction opposite to a forward direction in which the slide nut is interlocked with the plunger member, and determines whether the cartridge main body is a new cartridge main body or a previously used cartridge main body based on a detection signal of the attachment detection sensor.

8. The drug solution delivery apparatus according to claim 7, wherein:
in the new cartridge main body, the slide nut is disposed at a predetermined interval from the rib, and
when the cartridge main body is mounted on the pump main body, the controller causes the drive motor to rotate in a reverse direction by a predetermined amount.

9. The drug solution delivery apparatus according to claim 8, wherein:
the controller is programmed such that the number of rotations by which the drive motor is caused to rotate is set to be equal to or greater than the number of rotations of the drive motor until the slide nut attaches to the rib.

10. The drug solution delivery apparatus according to claim 8, wherein:
the controller is programmed such that, when it is determined that the cartridge main body is the previously used cartridge main body, the controller causes the drive motor to rotate in a forward direction by a predetermined amount or more.

11. The drug solution delivery apparatus according to claim 8, wherein:
the controller is programmed such that, when it is determined that the cartridge main body is the new cartridge main body, the controller causes the drive motor to rotate in a forward direction by a predetermined amount.

12. The drug solution delivery apparatus according to claim 7, wherein:
the attachment detection sensor is configured to detect rotation of the drive motor.

* * * * *